US012157000B2

(12) United States Patent
Grujic et al.

(10) Patent No.: US 12,157,000 B2
(45) Date of Patent: Dec. 3, 2024

(54) CARRYING CASE FOR CONTROLLER OF PATIENTS WITH VADS

(71) Applicant: Medtronic, Inc., Minneapolis, MN (US)

(72) Inventors: Luka Grujic, Boston, MA (US); Lance I. Farb, Miami, FL (US); Gerald M. Herman, Fridley, MN (US); Nicholas S. Difranco, New York, NY (US); Joseph Ippolito, Shoreview, MN (US); Timothy Hillukka, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 647 days.

(21) Appl. No.: 17/340,498

(22) Filed: Jun. 7, 2021

(65) Prior Publication Data

US 2021/0393945 A1    Dec. 23, 2021

Related U.S. Application Data

(60) Provisional application No. 63/042,644, filed on Jun. 23, 2020.

(51) Int. Cl.
*A45F 3/02*    (2006.01)
*A45F 5/00*    (2006.01)
*A61M 60/855*    (2021.01)

(52) U.S. Cl.
CPC .............. *A61M 60/855* (2021.01); *A45F 5/00* (2013.01); *A45F 2200/05* (2013.01); *A61M 2205/33* (2013.01); *A61M 2209/088* (2013.01)

(58) Field of Classification Search
CPC ........ A45F 2003/144; A45F 3/02; A45F 3/14; A45F 5/00; A45F 5/022; A45F 2003/025; A45C 11/00; A61M 60/855; A61M 2209/088; A61B 50/31
See application file for complete search history.

(56) References Cited

U.S. PATENT DOCUMENTS

| | | | | |
|---|---|---|---|---|
| 1,290,827 | A * | 1/1919 | Yergason | F42B 39/02 224/648 |
| 5,373,980 | A * | 12/1994 | Rowell | A45C 11/38 224/679 |
| 6,568,575 | B1 * | 5/2003 | Bartholomew | A45F 3/14 224/655 |
| 6,662,985 | B2 * | 12/2003 | Harada | G06F 1/1628 224/904 |

(Continued)

FOREIGN PATENT DOCUMENTS

| | | | |
|---|---|---|---|
| KR | 20110008183 U | * | 2/2010 |
| WO | 2012052999 A1 | | 4/2012 |

OTHER PUBLICATIONS

KR 20110008183 machine translation (Year: 2010).*
International Search Report and Written Opinion of International Application No. PCT/US2021/037162, dated Sep. 24, 2021, 9 pp.

*Primary Examiner* — Adam J Waggenspack
(74) *Attorney, Agent, or Firm* — Shumaker & Sieffert, P.A.

(57) ABSTRACT

A carrying case for a controller for an implantable blood pump includes a first flexible pouch sized and configured to retain the controller. The pouch has a first face and a second face opposite the first face, the first face includes a thermal insulating material and the second face including a thermal dissipating material.

19 Claims, 4 Drawing Sheets

(56) References Cited

U.S. PATENT DOCUMENTS

| | | | | |
|---|---|---|---|---|
| 8,807,412 | B2* | 8/2014 | Thomas | A61M 60/88 |
| | | | | 224/663 |
| 10,426,563 | B2* | 10/2019 | Dumesnil | A45F 3/02 |
| 10,544,502 | B2* | 1/2020 | Conolly | C23C 14/562 |
| 11,529,508 | B2* | 12/2022 | Jablonski | A45C 13/10 |
| 2003/0218038 | A1* | 11/2003 | Chang | A45F 5/02 |
| | | | | 224/675 |
| 2010/0122995 | A1 | 5/2010 | Thomas et al. | |
| 2017/0304017 | A1 | 10/2017 | Dumesnil | |
| 2019/0274873 | A1 | 9/2019 | Schoeggler et al. | |
| 2021/0401094 | A1* | 12/2021 | Clemens | A41D 13/1245 |

* cited by examiner

CARRYING CASE FOR CONTROLLER OF PATIENTS WITH VADS

CROSS-REFERENCE TO RELATED APPLICATION

This application claims the benefit of U.S. Application Ser. No. 63/042,644, filed Jun. 23, 2020.

FIELD

The present technology is generally related to a carrying case for a controller of an implantable medical device, and in particular, a controller for an implantable blood pump.

BACKGROUND

Implantable blood pumps are commonly used to assist the pumping action of a failing heart and typically include a housing with an inlet, an outlet, and a rotor mounted therein. The inlet may be connected to a chamber of the patient's heart, typically the left ventricle, using an inflow cannula. The outlet may be connected to an artery, such as the aorta. Rotation of the rotor drives blood from the inlet towards the outlet and thus assists blood flow from the chamber of the heart into the artery. A known type of blood pump is a ventricular assist device ("VAD") with examples including, but not limited to, the HVAD® pump and the MVAD® pump manufactured by HeartWare, Inc. in Miami Lakes, Fla., USA.

Such pumps include an external controller carried by the user. The external controller connects to a percutaneous driveline which extends out through the patient. Owing to the percutaneous connection, there is a length of driveline in addition to the controller that is carried by the user and can be unwieldy.

SUMMARY

The techniques of this disclosure generally relate to a carrying case for a controller of an implantable medical device, and in particular, a controller for an implantable blood pump.

In one aspect, a carrying case for a controller for an implantable blood pump includes a first flexible pouch sized and configured to retain the controller. The pouch has a first face and a second face opposite the first face, the first face includes a thermal insulating material and the second face including a thermal dissipating material.

In another aspect of this embodiment, the thermal insulating material is foam polymer In another aspect of this embodiment, the thermal dissipating material is a nylon mesh.

In another aspect of this embodiment, the case further includes a waist strap configured to engage the first pouch.

In another aspect of this embodiment, the case further includes a second pouch spaced a distance from the first pouch and engaged to the waist strap, the second pouch being sized and configured to retain a Smartphone.

In another aspect of this embodiment, the case further includes a shoulder strap configured to engaged the first pouch.

In another aspect of this embodiment, the case further includes at least one flap extending from the first pouch, the first flap including hook and loop fasteners.

In another aspect of this embodiment, the first pouch includes at least one window.

In another aspect of this embodiment, the thermally insulating material is substantially planar.

In another aspect of this embodiment, the second face is curved.

In one aspect, a carrying case for a controller for an implantable blood pump includes a first flexible pouch sized and configured to retain the controller, the pouch having a first face, a second face opposite the first face, a third face, and a fourth face opposite the third face, the first face being planar and including a thermal insulating material and the second face being curved and including a thermal dissipating material. A pair of flaps extends from the pouch, the pair of flaps including hook and loop fasteners.

In another aspect of this embodiment, a first of the pair of flaps extend in a first direction away from the first pouch and a second of the pair of flaps extend in a second direction opposite the first direction.

In another aspect of this embodiment, the pair of flaps are substantially co-planar with the first face.

In another aspect of this embodiment, the thermal insulating material is foam polymer.

In another aspect of this embodiment, the thermal dissipating material is a nylon mesh.

In another aspect of this embodiment, the case further includes a first waist strap configured to engage the first pouch.

In another aspect of this embodiment, the case further includes a second pouch spaced a distance from the first pouch and engaged to the waist strap, the second pouch being sized and configured to retain a Smartphone.

In another aspect of this embodiment, the case further includes a shoulder strap configured to engaged the first pouch.

In another aspect of this embodiment, at least one from the group consisting of the third face and the fourth face includes a window.

In one aspect, a carrying case for a controller for an implantable blood pump includes a first flexible enclosure sized and configured to retain the controller. The enclosure has a first face, a second face opposite the first face, a third face, and a fourth face opposite the third face. The first face is planar and includes a thermal insulating material and the second face is curved and including a thermal dissipating material. A pair of flaps extends away from the enclosure in opposite directions, the pair of flaps including hook and loop fasteners, the pair of flaps are substantially coplanar to the first face. A waist strap is coupled to the enclosure. A shoulder strap is coupled to the enclosure. At least one of the third face and the fourth face includes a window. A second enclosure is spaced a distance from the first enclosure and engaged to the waist strap, the second enclosure is sized and configured to retain a Smartphone.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
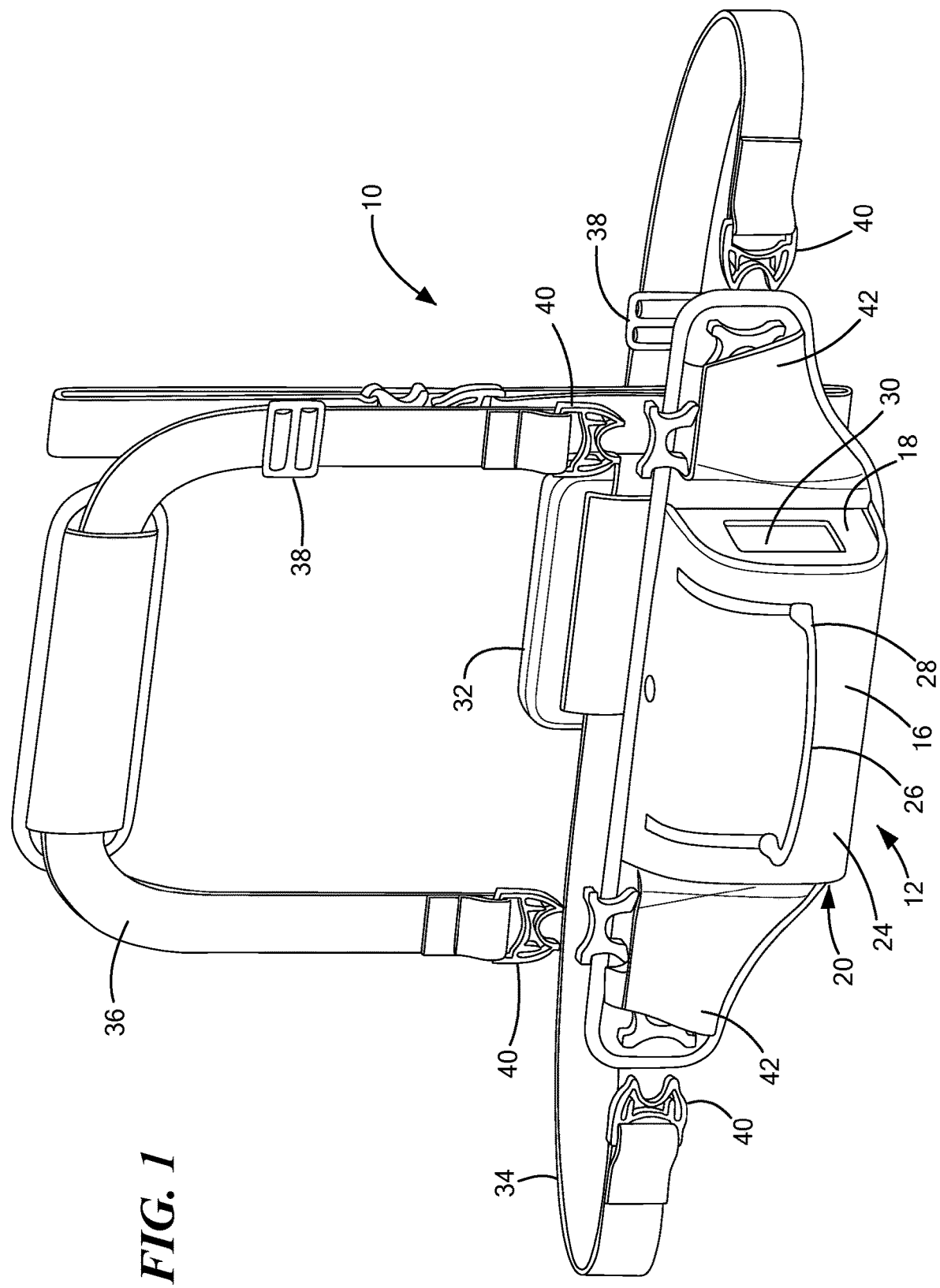
FIG. 1 is a front perspective view of a carrying case for a controller of an implantable blood pump constructed in accordance with the principles of the present application.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

Referring now to the drawings in which like reference designators refer to like elements there is shown in FIGS. 1-4 an exemplary carrying case for a controller for an implantable blood pump and designated generally as "10." The case 10 includes a first pouch 12 sized and configured to receive and retain a controller for an implantable blood pump. In one configuration, the pouch 12 is a soft enclosure and defines a length of between 8-12 inches and a height of between 4-7 inches and a thickness of 2-4 inches. The pouch 12 defines a first face 14 (shown in FIG. 2), a second face 16 opposite the first face 14, a third face 18, and a fourth face opposite the third face 18. The first face 14, which during use faces the user and is substantially planar, includes a thermally insulating material 22 (shown in FIG. 2) for example, nylon faced perforated PU or neoprene foam, to prevent the patient from being burnt from heat being given off by convection by the controller while the controller is working. In the configuration shown in FIG. 2, the thermally insulating material 22 is disposed on a planar portion of the first face 14 and may extend substantially the entire height of the first face 14. In other configurations, the entirety of the first face 14 may be composed of the thermally insulating material 22.

Continuing to refer to FIG. 1, the second face 16, which may be curved, for example, arcuate, is composed of a thermally transmissive material 24, for example, a nylon mesh or other open work fabric, such that heat may be convected away from the controller and the user. The second face 16 may include a zipper 26 extending from substantially the center of the second face 16 to a junction between the first face 14 and the second face 16. The zipper 26 may include two sets of teeth connected by a cord 28 to allow for easy opening and closing of the zipper 26. At least one of the third face 18 and the fourth face 20 may include a window 30 configured to allow the user to view the LCD display of the controller when received within the pouch 12. The windows 30 may be covered with a clear sheet of flexible plastic such that the pouch 12 remains soft. In one configuration, the windows 30 are planar and are symmetric about the pouch 12 such that if the controller is not in the pouch 12, a user can look through one window 30 and see through the opposite window 30. In other configurations, the window 30 defines a sleeve configured to receive a user's identification cards, credit cards, or other similar items.

Figure 2:
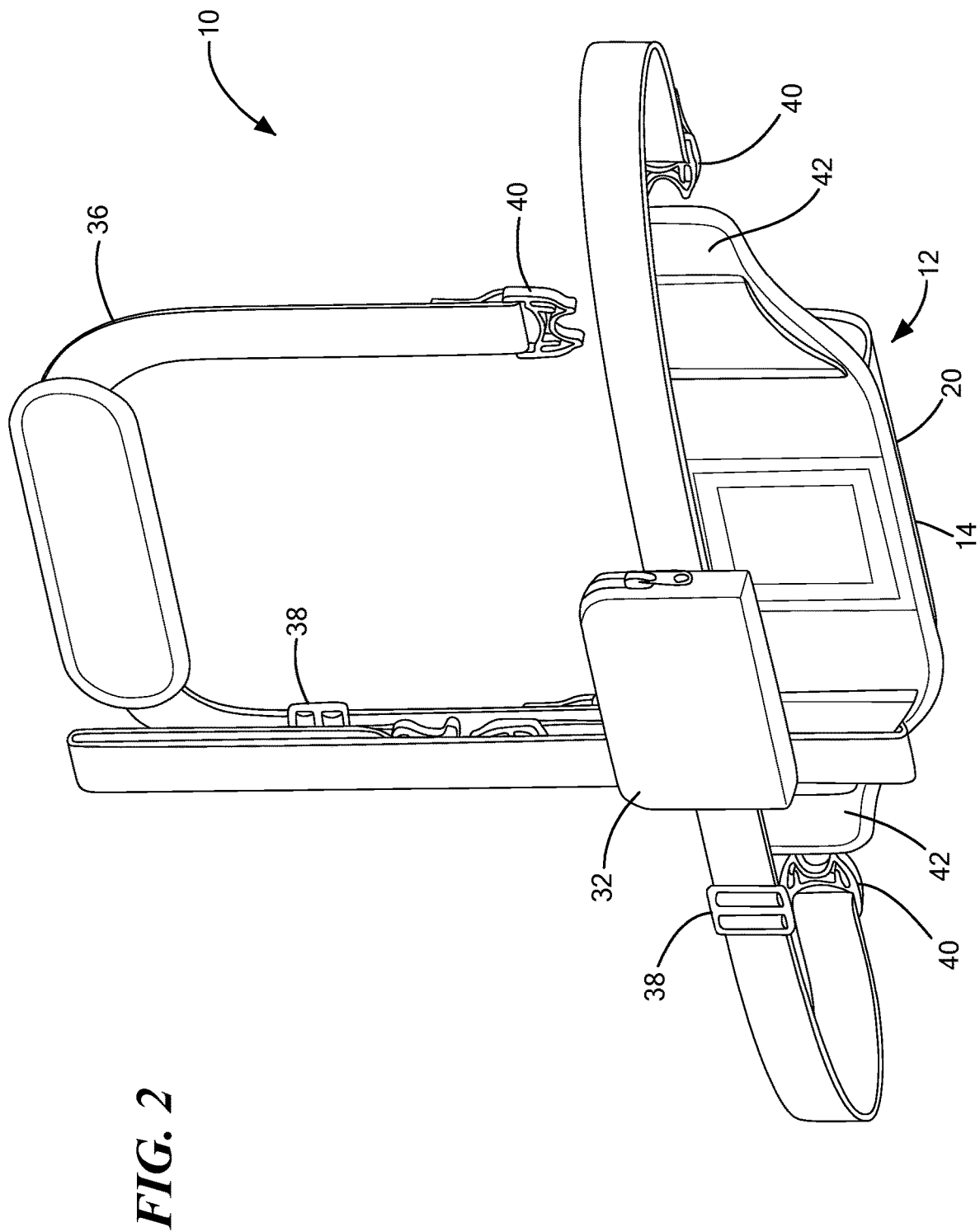
FIG. 2 is a back view of the carrying case shown in FIG. 1.
Figure 4:
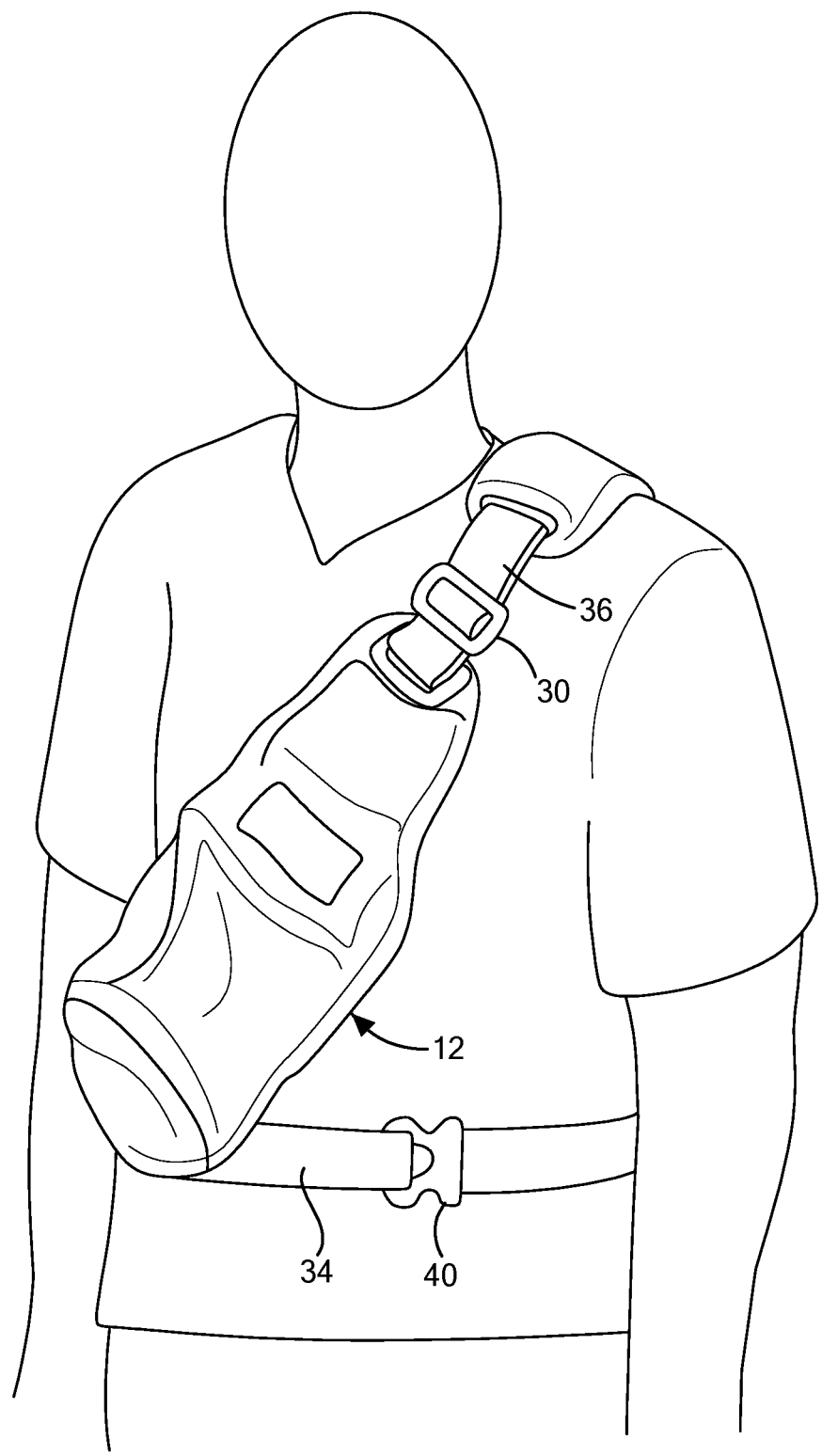
FIG. 4 is a front view showing a user wearing the carrying case shown FIG. 1 in an alternate configuration.

Continuing to refer to FIGS. 1-2, a second pouch 32 may be included as part of the case 10. The second pouch 32 is sized and configured to receive and retain a user's Smartphone, keys, or other items. The second pouch 32 is spaced a distance from the first pouch 12 to prevent electromagnetic interference between the Smartphone and the controller. In one configuration, the second pouch 32 is spaced 180 degrees from the first pouch 12 when worn around a user's waist. The first pouch 12 may be coupled to and otherwise engaged to waist strap 34 and/or a shoulder strap 36. The waist strap 34 and the shoulder strap 36 are both adjustable by one of more adjustment elements 38 and both include buckles 40, for example, squeeze buckles, that facilitate engagement of each respective strap 34, 36 to the pouch 12. In the configuration shown in FIGS. 1 and 2, the waist strap engages opposite ends of the pouch 12 and the shoulder strap 38 also engages opposite portions of the pouch 12. In one configuration the female ends of buckles 40 are disposed at 90 degrees from each other and are adjacent each other when engaged to allow for easy opening and closing of each buckle 40. The user can optionally remove one of the waist or shoulder straps 34 and 36 and where one or the other. For example, the user can wear just one of the shoulder straps 36 or uncouple one of the buckles 40 to wear the pouch 12 over just one of the user's shoulders, as shown in FIG. 4. Moreover, additional straps may be included to increase the size of any one of the waist or shoulder straps 34 and 36. For example, an additional shoulder strap 36 may be included and coupled to the back of the shoulder strap 36.

Figure 3:
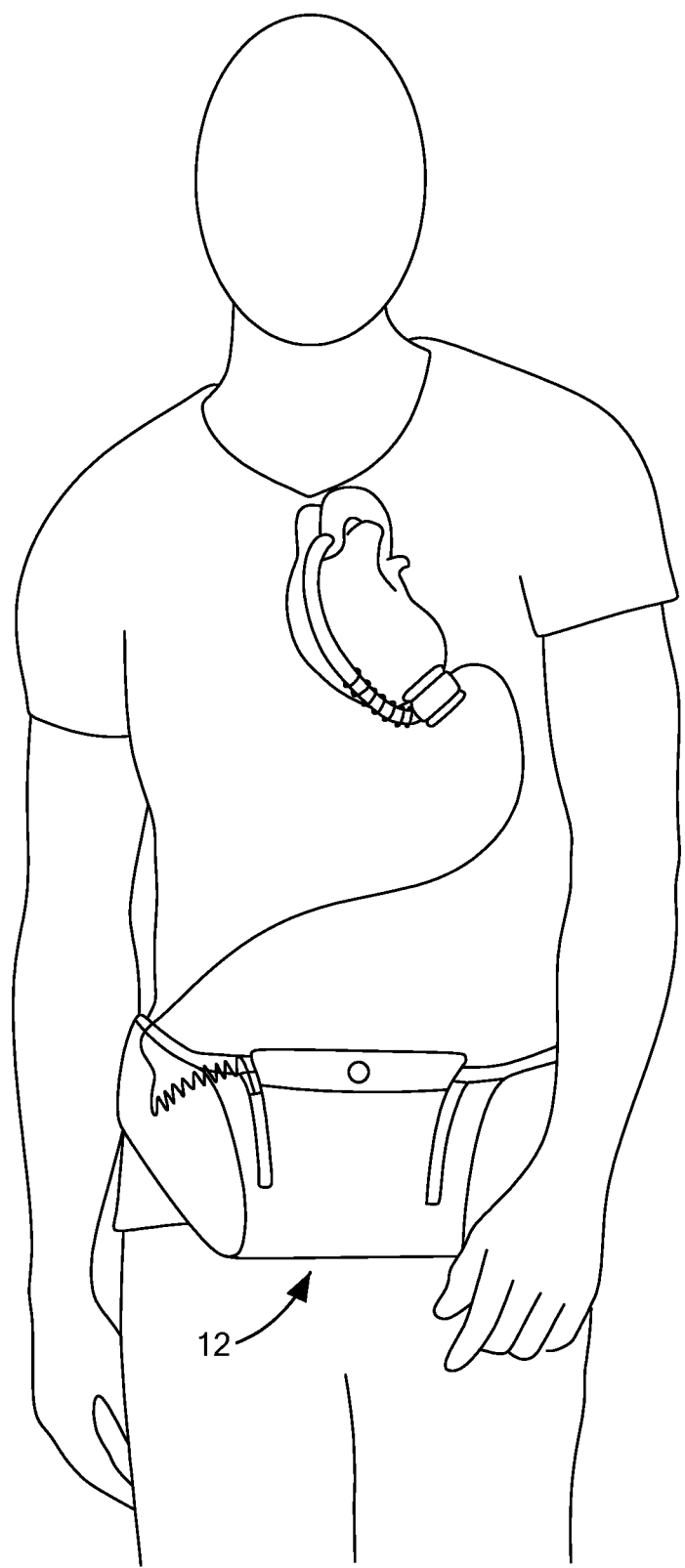
FIG. 3 is a front view showing a user wearing the carrying case shown in FIG. 1.

Referring now to FIGS. 1-3, at least one flap 42 extends from the pouch 12 and is configured to maintain or otherwise manage a length of driveline extending from the patient to the controller. For example, as shown in FIG. 3, the at least one flap 42 is shown in a closed position in which a length of driveline cable is disposed within the flap 42 such that movement of the user does not pull on the driveline and cause discomfort. FIG. 1 further shows the flaps 42 in an open and closed position. In this configuration, the buckles 40 extend away from the flaps 42 such that they are accessible when the flaps are closed. Moreover, in the closed position, the flaps 42 extend substantially planar with the first face 14 of the pouch 12. In the open position, the user engages the driveline within the flaps 42 and engages the respective flap 42 on itself with a hook and loop fastener disposed within the respective flap 42.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A carrying case for a controller for an implantable blood pump, the carrying case comprising:
   a flexible pouch sized and configured to retain the controller, the flexible pouch defining a first face defining a first edge and a second edge opposite the first edge, a second face opposite the first face and curved between the first edge and the second edge, the second face defining a third edge and a fourth edge, a third face extending between the first face and the third edge of the second face, and a fourth face opposite the third face and extending between the first face and the fourth edge of the second face, wherein the first face includes a thermally insulating material, and wherein the second face includes a thermally transmissive material.

2. The case of claim 1, wherein the thermally insulating material is perforated polyurethane or neoprene foam.

3. The case of claim 1, wherein the thermally transmissive material is a nylon mesh.

4. The case of claim 1, further including a waist strap configured to engage the flexible pouch.

5. The case of claim 4, wherein the flexible pouch is a first pouch, the case further including a second pouch spaced a distance from the first pouch and engaged to the waist strap, the second pouch being sized and configured to retain a smartphone.

6. The case of claim 5, further including a shoulder strap configured to engage the first pouch.

7. The case of claim 1, further including at least one flap extending from the flexible pouch, the at least one flap including hook and loop fasteners.

8. The case of claim 1, wherein the third face defines at least one window.

9. The case of claim 8, wherein the thermally insulating material is substantially planar.

10. A carrying case for a controller for an implantable blood pump, the carrying case comprising:
a flexible pouch sized and configured to retain the controller, the flexible pouch defining a first face defining a first edge and a second edge opposite the first edge, a second face opposite the first face and curved between the first edge and the second edge, the second face defining a third edge and a fourth edge, a third face extending between the first face and the third edge of the second face, and a fourth face opposite the third face and extending between the first face and the fourth edge of the second face, the first face being planar and including a thermally insulating material and the second face including a thermally transmissive material; and
a pair of flaps extending from the flexible pouch, the pair of flaps including hook and loop fasteners.

11. The case of claim 10, wherein a first flap of the pair of flaps extends in a first direction away from the flexible pouch and a second flap of the pair of flaps extends in a second direction opposite the first direction.

12. The case of claim 11, wherein each flap of the pair of flaps is substantially co-planar with the first face.

13. The case of claim 10, wherein the thermally insulating material is perforated polyurethane or neoprene foam.

14. The case of claim 10, wherein the thermally transmissive material is a nylon mesh.

15. The case of claim 10, further including a waist strap configured to engage the flexible pouch.

16. The case of claim 15, further including a second pouch spaced a distance from the flexible pouch and engaged to the waist strap, the second pouch being sized and configured to retain a smartphone.

17. The case of claim 16, further including a shoulder strap configured to engage the flexible pouch.

18. The case of claim 10, wherein at least one of the third face or the fourth face defines a window.

19. A carrying case for a controller for an implantable blood pump, the carrying case comprising:
a first flexible enclosure sized and configured to retain the controller, the first flexible enclosure defining a first face defining a first edge and a second edge opposite the first edge, a second face opposite the first face and curved between the first edge and the second edge, the second face defining a third edge and a fourth edge, a third face extending between the first face and the third edge of the second face, and a fourth face opposite the third face and extending between the first face and the fourth edge of the second face,
the first face being planar and including a thermally insulating material and the second face including a thermally transmissive material;
a pair of flaps extending away from the first flexible enclosure in opposite directions, the pair of flaps including hook and loop fasteners, each flap of the pair of flaps being substantially coplanar to the first face;
a waist strap coupled to the first flexible enclosure;
a shoulder strap coupled to the first flexible enclosure,
at least one of the third face or the fourth face defining a window; and
a second enclosure spaced a distance from the first flexible enclosure and engaged to the waist strap, the second enclosure being sized and configured to retain a smartphone.

* * * * *